United States Patent [19]

Suzuki et al.

[11] Patent Number: 5,283,059
[45] Date of Patent: Feb. 1, 1994

[54] PROCESS FOR PRODUCING A STABILIZED STORE-FORMING VIABLE MICROORGANISMS PREPARATION CONTAINING *BACILLUS CEREUS*

[75] Inventors: Masaki Suzuki; Hideyuki Yamaoka; Mutsumi Aoshima; Koji Hashimoto, all of Shizuoka, Japan

[73] Assignee: Asahi Kasei Kogyo Kabushiki Kaisha, Asaka, Japan

[21] Appl. No.: 867,527

[22] Filed: Apr. 13, 1992

Related U.S. Application Data

[62] Division of Ser. No. 529,727, May 23, 1990, abandoned.

[30] Foreign Application Priority Data

May 24, 1989 [JP] Japan ................................ 1-130580
Mar. 6, 1990 [JP] Japan ................................ 2-54711

[51] Int. Cl.$^5$ ............................................. A61K 37/00
[52] U.S. Cl. ............................. 424/93 K; 435/252.5; 435/260; 435/832; 435/834; 426/61
[58] Field of Search ................... 435/260, 252.5, 831, 435/833, 834, 835, 838, 839, 836; 424/93 L-93 N, 93 K; 426/60, 61, 62

[56] References Cited

U.S. PATENT DOCUMENTS

| | | | |
|---|---|---|---|
| 2,744,015 | 5/1956 | Katsube et al. | 424/93 |
| 3,655,396 | 4/1972 | Goto et al. | 426/60 |
| 3,911,110 | 10/1975 | Smirnoff | 424/93 |
| 4,081,557 | 3/1978 | Azoulay | 426/60 |
| 4,996,055 | 2/1991 | Kurasawa | 435/839 |
| 5,147,640 | 9/1992 | Gard et al. | 424/93 L |

FOREIGN PATENT DOCUMENTS 0126642 9/1988 Australia.
0257996 9/1988 European Pat. Off..

*Primary Examiner*—Marian Knode
*Attorney, Agent, or Firm*—Young & Thompson

[57] ABSTRACT

A stabilized spore-forming viable microorganism composition comprising in admixture at least a carbohydrate component from cereals or bulbs and spore-forming viable microorganisms belonging to genus Bacillus. Examples of cereals are maize, rice, wheat, barley, rye, oats and soybeans. Examples of bulbs are tuberous roots, tubers or corms. That component can also be a polysaccharide, e.g. starch. At least over 0.01 part by weight of the carbohydrate component is used per one part by weight of microorganisms. A process for production of the composition comprises drying a carbohydrate component from cereals or bulbs and spore-forming viable microorganisms belonging to genus Bacillus in admixture in a non-toxic aqueous medium.

7 Claims, No Drawings

PROCESS FOR PRODUCING A STABILIZED STORE-FORMING VIABLE MICROORGANISMS PREPARATION CONTAINING BACILLUS CEREUS

This application is a division of application Ser. No. 07/529,727 filed May 23, 1990, now abandoned.

FIELD OF THE INVENTION

This invention relates to a stabilized spore-forming viable microorganism composition, a process for its production, and a pellet embodying the same.

THE PRIOR ART

A viable microorganism-containing feed is a feed in which viable useful microorganisms are admixed with feed, and is frequently used for the prevention and treatment of animal diseases or improvement of animal health An enteric bacterium, Bifidobacterium viable in the intestine, is known to play an important role in the prevention of intestinal infection, intestinal putrefaction and diarrhea, and foods and feeds to which has been added viable Bifidobacteria are available commercially.

A bacterium belonging to genus Bacillus is also known to be useful, and feeds containing these bacteria are known. In these viable microorganism compositions, various ingredients are added for stability of bacterial viability over the term of production, distribution and consumption of the foods and feeds, namely for providing a viable stage in vivo in human or animal bodies.

As for Bifidobacterium compositions, it is known that a preparation with added asparagine or sodium glutamate or soluble starch is storable at high temperature (Japanese Patent Publ. No. 43-3889)

Further known is a gastric-acid-stable viable Bifidobacterium powder which comprises in admixture skim milk, starch hydrolysate, sodium glutamate, sodium ascorbate, magnesium salt and a cultured medium of Bifidobacterium which is lyophilized (Japanese Patent Unexam. Publ No. 60-188060)

There is also known a process for preparing a powdered composition containing active Bifidobacteria which is storable for a long term at ambient temperature, which comprises mixing wetted or suspended Bifidobacteria and raw starch and lyophilizing (Japanese Patent Unexam. Publ. No. 63-12594) the mixture, or a process for preparing a powder preparation containing Bifidobacteria which is storable for a long term at ambient temperature and can be kept with few deaths of viable microorganisms despite drying, granulation and storage, which comprises suspending the wetted or suspended cells of Bifidobacterium in the dispersion medium containing soluble cyclodextrin and drying the same to a powder (Japanese Patent Unexam. Publ. No. 63-251080).

There is also known, although not as a food or feed, the preparation of stable and active viable microorganisms which comprises adsorbing viable mycelia of Fusarium to a zeolite-type base and drying, or suspending the viable mycelia in a dispersion medium containing D-sorbitol added thereto with a small amount of glutamate salt, the mixture then being lyophilized (Japanese Patent Unexam. Publ. No. 63-227507).

Spore-forming viable microorganisms such as genus Bacillus are relatively stable under dry and acid conditions by sporulation and also are useful as viable microorganisms, and are used as such in feed (Japanese Patent Unexam. Publ. No. 53-6211). Among these, Toyocerin (trade name, *Bacillus cereus* var. toyoi, generic abbreviation *Bacillus toyoi*), Laclis (trade name, *Bacillus coagulans*), Glogen (trade name, *Bacillus subtilis* var. natto), Paciflor (trade name, *Bacillus cereus* IP-5832) and Bioplus 2B (trade name, *Bacillus licheniformis, Bacillus subtilis*) are known.

BACKGROUND OF THE INVENTION

A viable microorganism composition is needed for addition to mixed feed in order to increase growth and improve feed efficiency of livestock by maintaining a balance of intestinal microbial flora which plays an important role in nutritional actions such as the metabolism of nutrients and the synthesis of vitamins. Viable microorganism compositions can be effective only if they reach the digestive tract, and hence stability in storage feed and stability under acid and alkaline conditions and under heating are essential. Spore-forming viable microorganisms belonging to genus Bacillus are preferably used for that purpose.

Pellet-type feed has a number of advantages: for example, each pellet is a complete feed unit with homogenized feed components. The availability of nutrients in the feed is increased. The palatability of the feed is improved. Body weight gain and feed efficiency are improved. The feed is less bulky and so is easy to handle. Feeding time and labor can be saved, and the waste of feed by blowing off in the wind and spilling is minimized. As a result of these advantages pellet-type feed is quite popular. Since the pellets are manufactured by formulating previously pulverized feed components and pelleting with pressure and steam by means of a pelletmill, even the relatively heat stable spore-forming microorganisms such as genus Bacillus are partially destroyed and lose viability due to the effects of steam heating, generated heat, pressure and water content; and hence there is the disadvantage that a large proportion of the viable microorganisms is lost.

SUMMARY OF THE INVENTION

In order to manufacture pellet-type feed of stabilized spore-forming viable microorganisms belonging to genus Bacillus, we have made a number of experiments on pelleting in combination with previously known stabilizing agents for Bifidobacteria and other viable microorganisms and sporeforming viable microorganism compositions, and have measured the viable counts, and have tried to obtain stable sporeforming viable microorganism compositions. However, suitable results could not be obtained due to the death of microorganisms because of heating and pressure during the pelleting process.

We have found quite surprisingly that in the spore-forming compositions containing viable microorganisms belonging to genus Bacillus, the combination of spray-drying or kneading-blow drying and the admixture of a carbohydrate component originating from cereals or bulbs results in an increase in viable counts following the pelleting process of producing feed for livestock.

OBJECT OF THE INVENTION

An object of the present invention is accordingly to provide a stabilized spore-forming viable microorganism composition comprising a carbohydrate component originating from cereals or bulbs and spore-forming viable microorganisms belonging to genus Bacillus, and to provide a process for its production and pellets resulting therefrom.

DETAILED DESCRIPTION OF THE INVENTION

Examples of spore-forming viable microorganisms can be any microorganisms belonging to genus Bacillus which can be used for feed, and are *Bacillus toyoi* (trade name Toyocerin), *Bacillus coagulans* (trade name Lacclis), *Bacillus subtilis* var. natto (trade name Glogen), *Bacillus cereus* IP-5832 (trade name Paciflor) and *Bacillus licheniformis* and *Bacillus subtilis* (trade name Bioplus 2B). A preferred example is a microorganism belonging to *Bacillus cereus* and more preferably *Bacillus toyoi*.

In this context, the term bulb mans a part of a root or an enlarged subterranean stem of plants, the enlargement providing storage for nutrients, and includes tuberous roots, tubers and corms. Examples of bulbs are tuberous roots such as sweet potatoes (*Ipomoea batatas*), tubers such as potatoes (*Solanum tuberosum*), and corms such as taro (*Colocasia antiguorum*).

Examples of carbohydrate component originating from cereals used for a base in viable microorganism compositions of the present invention are maize (Indian-corn or corn) powder per se, for example crushed or powdered kernels of maize (*Zea mays* Linne (Gramineae)) optionally dried, and include commercially available corn flour (powdered corn) and corn grits (Indian meal, hominy, corn meal).

The other examples of carbohydrate from cereals are components from rice, for example defatted rice bran, namely a defatted, dried and if necessary crushed mixture of seed coat, albumen and starch layer of threshed seeds of rice plants (*Oryza sativa* Linne (Gramineae)) obtained from rice polishing.

Examples of starch are maize starch (cornstarch), rice starch, wheat starch, potato starch and sweet potato starch. These are mixtures of amylose and amylopectin, and hence any starch obtained from cereals and bulbs can be used.

An example of wheat flour is crushed and optionally dried grains of *Triticumsativum Lamarck* (Gramineae) and comprises wheat middling or wheat bran.

An example of carbohydrate from soybean is, for example crushed and optionally dried beans of *Glycine max* Merrill (Leguminosae) and comprises defatted soybean flour, soybean meal, soybean mill-run or soybean cake.

These bases can be used, for example by mixing one or more kinds of the base with spore-forming viable microorganisms to prepare an aqueous suspension, then spray-drying the suspension after pre-heating, for example to above 60°-75° C., the gelatinization temperature of the starch component of maize, or without a pre-heating treatment, or by kneading the mixture and then drying with blowing. The dried mixture of the base and spore-forming viable microorganisms is pulverized in a crushing mill such as a spread-mill and granulated in an oscillating granulator to prepare a dried powder which is a viable microorganism composition. A carbohydrate component from cereals or bulbs such as rice bran, starch, wheat flour, soybean flour, sweet potato, potato or taro can also be used by mixing the suspension thereof directly or the pre-heated gelatinized component thereof with spore-forming viable microorganisms, then spray-drying or kneading and blow-drying.

The above exemplified base used in the present invention has a stabilizing effect on microorganisms in a spore-forming viable microorganism composition used for pellet production, although the effect is slightly different depending on the kind of base and drying conditions and whether spray-drying or blow-drying is performed with an aqueous suspension or with heat-gelatinization. However any drying process provides the stabilizing effect which can be obtained by the heat-gelatinization of starch.

The viable microorganism composition feed obtained by mixing the dried powder viable microorganism composition with animal feed or fish feed is pelleted by a conventional method using a pelleting machine to obtain pellet-type feed. Admixed feed and other ingredients can be selected according to the kind of livestock, poultry or fish.

The mixing ratio of the base, i.e. components from maize or defatted rice bran, starch, wheat powder, soybean flour and component from bulbs, and spore-forming viable microorganisms is at least 0.01 part by weight of the base per one part by weight of microbial cells, usually 0.01-100 parts by weight, preferably 0.1-10 parts by weight. Viable counts of approximately $10^{13}$-$10^{15}$ cells are contained in 1 kg of microbial cells.

The pelleting of viable microorganism composition feed can be carried out by a conventional pelleting method. A mixture of dried powder of viable microorganism composition and formula feed or ingredient is pelleted using a pellet mill (e.g. Type J10, Jooda Iron Work Co.) Pellet feed can be produced by using dies for pelleting while supplying steam and thereafter drying. The hardness and size of the pellets should be selected according to the kind of animal feed. For example, in Japan, the hardness of the pellet is; soft type for chickens, i.e. Monsant hardness approx. 2-5 kg; medium type for swine, i.e. Monsant hardness approx. 5-7 kg; and hard type for rabbits, i.e. Monsant hardness approx. 2-12 kg. These feeds for livestock, poultry, and other animals and fish are formed as pellets.

During the pelleting process, a considerable number of viable microorganisms admixed in feeds are burst and heat-denatured due to hardening of the pellet by steam and high pressure. In the case of pelleting of conventional spray-dried spore-forming viable microorganisms belonging to genus Bacillus, the viable count is reduced to approx. 30% at high hardness, although viability depends on the hardness of the pellets prepared. On the contrary, a viable microorganism composition prepared by spray-drying with admixture of the base of the present invention results in over 80% viable count.

Accordingly, even for a pellet hardness of 8-10 kg, a viable count over 70%, preferably over 80%,is considered to be an advantageously improved stability.

With a spore-forming viable microorganism composition of the present invention, which is a powdered mixture of spore-forming viable microorganisms, preferably spore-forming viable microorganisms belonging to genus Bacillus and a carbohydrate component originating from cereals or bulbs such as maize flour, defatted rice bran, starch, what flour and soybean flour, it is possible to maintain substantially the same viable count of microorganisms after the pelleting process as before pelleting with admixed feed for livestock or fish or veterinary drug. Hence the present invention is easy and economical to use when preparing feed. The spore-forming viable microorganism composition of the present invention can be used to achieve, for example $0.2$–$2\times10^6$ cells/kg feed weight for animal feed, $0.2$–$1\times10^7$ cells/kg feed weight for fish feed, and $5\times10^6$–$2\times10^8$ cells/kg feed weight for veterinary drugs.

EXAMPLES

The following examples illustrate the present invention but are not to be construed as limiting the scope thereof.

EXAMPLE 1

A viable cell spore suspension of *Bacillus toyoi* (Toyocerin) (cell count: $2.1\times10^{10}$ cell/ml; microbial cells 10%) was suspended with corn flour (Sunny Maize Co.) as set forth in Table 1, and spray-dried by means of a spray-dryer (KC-50, Ohkawara Kakoki Co.) to obtain a powdered viable microorganism composition.

Spray-drying: intake temperature —150° C., outlet temperature —90° C.;

atomizer: 10,000 rpm.

For control group 1, Toyocerin is mixed with calcium carbonate powder (Korocalso-WB, trade name, Shiraishi Calcium Co.) and spray-dried to obtain the product "Control-1".

TABLE 1

| Sample No. | cell suspension (l) (): cell weight (kg) | Base (kg) | Ratio of base:cell weight | Viable count in dried powder (cells/g) |
|---|---|---|---|---|
| 1-a | 20(2) | 2 | 1:1 | $9.11\times10^{10}$ |
| 1-b | 20(2) | 1 | 1:0.5 | $13.9\times10^{10}$ |
| 1-c | 20(2) | 0.2 | 1:0.1 | $17.7\times10^{10}$ |
| 1-d | 20(2) | 0.02 | 1:0.01 | $19.5\times10^{10}$ |
| Control-1 | 20(2) | 10 | 1:5 | $3.0\times10^{10}$ |

EXAMPLE 2

The samples obtained in Example 1 were mixed uniformly with feed at a viable microorganism count of approx. $1.1\times10^6$ cells per gram to prepare a mash. Pellets were prepared using a pellet-mill (Jooda Iron Work Co., Type J10), with a die diameter of 3.5 mm, with the supply of steam, and the moist pellets were then dried to obtain the pellet product. The stability of the viable microorganisms was checked by counting them in the pellet sand comparing that count with the count in the mash. Since the hardness of the pellets depends on the type of feed, the hardness was selected at the following three levels: hardness—high: (A) feed for rabbits (NRT1S, Nisseiken Co.), hardness—medium: (B) feed for swine (synthetic milk for late term, Nihon Haigo Shiryo Co.) and hardness—somewhat low: (C) feed for chickens (chicken feed, Nihon Haigo Shiryo Co.)

The hardness of the pellets was measured using a Monsant hardness meter. The results are shown in Table 2, in which sample 1-d —viable counts, slightly improved; and samples 1-a, 1-b and 1-c—viable counts, significantly improved, are to be compared with a decrease in the viable count in the control after pelleting. Specifically, the high hardness pellets show a significant improved viable count.

Accordingly, the stability of viable microorganisms in the pelleting process with feed was shown to be significantly improved in the powdered composition obtained by spray-drying the mixture of corn flour in excess of 0.01 part, preferably over 0.1 part per one part by weight of microbial cells.

TABLE 2

| Sample No. | Feed | Pellet hardness (kg) | Viable count in mash (cells/g) | Viable count in pellet (cells/g) | Viable ratio (%) |
|---|---|---|---|---|---|
| 1-a | A | 8.9 | $1.29\times10^6$ | $1.13\times10^6$ | 88 |
|  | B | 7.4 | $1.33\times10^6$ | $1.13\times10^6$ | 85 |
|  | C | 3.3 | $1.32\times10^6$ | $1.27\times10^6$ | 96 |
| 1-b | A | 9.6 | $1.01\times10^6$ | $0.807\times10^6$ | 80 |
|  | B | 5.8 | $1.17\times10^6$ | $0.958\times10^6$ | 82 |
|  | C | 3.9 | $1.06\times10^6$ | $1.06\times10^6$ | 100 |
| 1-c | A | 9.6 | $1.28\times10^6$ | $1.10\times10^6$ | 86 |
|  | B | 5.7 | $1.19\times10^6$ | $1.17\times10^6$ | 98 |
|  | C | 4.2 | $1.28\times10^6$ | $1.14\times10^6$ | 89 |
| 1-d | A | 9.2 | $1.13\times10^6$ | $0.659\times10^6$ | 58 |
|  | B | 7.2 | $1.06\times10^6$ | $0.704\times10^6$ | 66 |
|  | C | 4.0 | $1.10\times10^6$ | $0.968\times10^6$ | 88 |
| Control-1 | A | 9.1 | $1.05\times10^6$ | $0.359\times10^6$ | 34 |
|  | B | 6.2 | $1.01\times10^6$ | $0.548\times10^6$ | 54 |
|  | C | 3.9 | $1.32\times10^6$ | $1.03\times10^6$ | 78 |

EXAMPLE 3

Corn flour samples (each 2 g and 20 g, respectively) suspended in water (200 ml) was pre-gelatinized by being heated at 85° C. The gelatinized liquid was cooled and kneaded well with admixed cells of Bacillus toyoi (20 g, $2.1\times10^{10}$ cells/g), then spread on a plate and dried by blowing at room temperature or at 80° C. The dried product was crushed in a speed mill and subsequently granulated in an oscillating granulator (32 mesh, oscillator) to prepare viable microorganism compositions.

Further corn flour (20 g) suspended in water (200 ml) was mixed with microbial cells (20 g) and kneaded to prepare the composition. The results are shown in Table 3.

TABLE 3

| Sample No. | Cell weight (g) | Base (cornflour) weight (g) | Base (cornflour) condition of liquid | Ratio of base:cell weight | Blow-drying | Viable count in dried powder (cells/g) |
|---|---|---|---|---|---|---|
| 3-a | 20 | 20 | paste | 1:1 | room temp. | $7.2\times10^{10}$ |
| 3-b | 20 | 2 | paste | 1:0.1 | room temp. | $13.5\times10^{10}$ |
| 3-c | 20 | 20 | paste | 1:1 | 80° C. | $6.4\times10^{10}$ |
| 3-d | 20 | 20 | suspension | 1:1 | room temp. | $7.4\times10^{10}$ |

EXAMPLE 4

Samples obtained in Example 3 were pelleted by the same process as in Example 2. The viable count was measured and compared with that of the mash for checking the stability of the viable microorganisms.

The results are shown in Table 4. The stability of samples 3-a, 3-b and 3-c, which were prepared by admixture with a pasty liquid of pre-heated gelatinized corn flour, was observed to be improved as compared with control samples in the pelleting process. By contrast sample 3-d, which was prepared only by suspending corn flour in water and drying, was observed to be unstable. Accordingly, in the case of corn flour, the use of a pasty gelatinized liquid thereof produced by heat treatment was preferable with regard to the stability of the viable microorganism cells.

TABLE 4

| Sample No. | Feed | pellet hardness (kg) | Viable of count in mash (cells/g) | Viable count in pellet (cells/g) | Viable ratio (%) |
|---|---|---|---|---|---|
| 3-a | A | 8.4 | $1.22 \times 10^6$ | $1.10 \times 10^6$ | 90 |
|  | B | 7.0 | $1.18 \times 10^6$ | $1.20 \times 10^6$ | 102 |
|  | C | 4.2 | $1.37 \times 10^6$ | $1.32 \times 10^6$ | 96 |
| 3-b | A | 11.2 | $1.30 \times 10^6$ | $1.12 \times 10^6$ | 86 |
|  | B | 6.8 | $1.26 \times 10^6$ | $1.20 \times 10^6$ | 95 |
|  | C | 4.8 | $1.21 \times 10^6$ | $1.24 \times 10^6$ | 102 |
| 3-c | A | 9.4 | $1.28 \times 10^6$ | $1.01 \times 10^6$ | 79 |
|  | B | 5.8 | $1.14 \times 10^6$ | $0.988 \times 10^6$ | 87 |
|  | C | 3.9 | $1.03 \times 10^6$ | $1.08 \times 10^6$ | 105 |
| 3-d | A | 10.9 | $1.17 \times 10^6$ | $0.510 \times 10^6$ | 44 |
|  | B | 7.4 | $1.12 \times 10^6$ | $0.704 \times 10^6$ | 63 |
|  | C | 4.1 | $1.04 \times 10^6$ | $0.973 \times 10^6$ | 94 |
| Contorl-1 | A | 9.1 | $1.05 \times 10^6$ | $0.359 \times 10^6$ | 34 |
|  | B | 6.2 | $1.01 \times 10^6$ | $0.548 \times 10^6$ | 54 |
|  | C | 3.9 | $1.32 \times 10^6$ | $1.03 \times 10^6$ | 78 |

EXAMPLE 5

Defatted rice bran (Nihon Seimaiseiyu Co.) was suspended or kneaded with a cell-suspension of *Bacillus toyoi* ($2.1 \times 10^{10}$ cells/ml; microbial cells 10%) at the composition shown in Table 5, and spray-dried according to the process in Example 1 or blow-dried according to that in Example 3 to obtain powdered viable microorganism compositions.

TABLE 5

| Sample No. | Cell suspension (l) (): cell weight (kg) | Base (kg) | Ratio of cells: base | Drying Method | Viable count in dried powder (cells/g) |
|---|---|---|---|---|---|
| 5-a | 0.2 (0.02) | 0.02 | 1:1 | room temp. blow-drying | $7.5 \times 10^{10}$ |
| 5-b | 0.2 (0.02) | 0.02 | 1:1 | 80° C. blow-drying | $7.2 \times 10^{10}$ |
| 5-c | 10 (1) | 1 | 1:1 | spray-drying | $9.6 \times 10^{10}$ |

EXAMPLE 6

Pellets of samples of Example 5 were produced by the same process as in Example 2. The viable count was measured and compared with that of the mash for checking the stability of the viable microorganisms.

The results are shown in Table 6. The stability of the powdered viable microorganism composition using defatted rice bran produced by blow-drying and spray-drying in the pelleting process was not decreased and was superior. Accordingly rice bran was observed to provide a degree of stability of viable microorganisms in the pelleting process as high as that of corn flour.

TABLE 6

| Sample No. | Feed | Pellet hardness (kg) | Viable count in mash (cells/g) | Viable count in pellet (cells/g) | Viable ratio (%) |
|---|---|---|---|---|---|
| 5-a | A | 9.6 | $1.23 \times 10^6$ | $1.11 \times 10^6$ | 90 |
|  | B | 7.3 | $1.16 \times 10^6$ | $1.05 \times 10^6$ | 91 |
|  | C | 4.8 | $1.30 \times 10^6$ | $1.31 \times 10^6$ | 101 |
| 5-b | A | 8.1 | $1.18 \times 10^6$ | $0.944 \times 10^6$ | 80 |
| 5-c | A | 8.2 | $1.18 \times 10^6$ | $1.02 \times 10^6$ | 86 |
|  | B | 4.8 | $1.09 \times 10^6$ | $1.04 \times 10^6$ | 95 |

EXAMPLE 7

Starch (cornstarch, Wako Pure Chem. Co.) was suspended in a spore-cell suspension of *Bacillus toyoi* (Toyocerin, $2.7 \times 10^{10}$ cells/ml; microbial cells 10%) at the composition illustrated in Table 7, and spray-dried using a spray-dryer (Ohkawara Kakoki Co., Type KC-50) to obtain powdered viable microorganism compositions.

Spray-drying: intake temperature—150° C., outlet temperature—90° C.;
atomizer: 10,000 rpm.

For control group 2, Toyocerin is mixed with calcium carbonate powder (korocalso-WB, trade name, Shiraishi Calcium Co.) and spray-dried to obtain the product "Control-2".

TABLE 7

| Sample No. | Cell suspension (l) (): cell weight (kg) | Base (kg) | Ratio of cell: base | Viable count in dried powder (cells/g) |
|---|---|---|---|---|
| 7-a | 10 (1) | 1 | 1:1 | $12.6 \times 10^{10}$ |
| 7-b | 10 (1) | 0.5 | 1:0.5 | $14.9 \times 10^{10}$ |
| 7-c | 10 (1) | 0.1 | 1:0.1 | $17.0 \times 10^{10}$ |
| 7-d | 10 (1) | 0.01 | 1:0.01 | $17.4 \times 10^{10}$ |
| Control-2 | 10 (1) | 5 | 1:5 | $3.0 \times 10^{10}$ |

EXAMPLE 8

The samples obtained in Example 7 were mixed uniformly with feed at a viable cell count of approx. $1.1 \times 10^6$ cells per gram to prepare a mash. Pellets were prepared using a pellet-mill (Jodda Iron Work Co., Type J10 having a die diameter of 3.5 mm, with the supply of steam; then the pellets were dried to obtain the pelleted product. The stability of the viable microorganisms was checked by counting the viable microorganisms in the pellets as compared with those in the mash. Since the hardness of the pellet depends on the type of feed, the hardness was selected at the following three levels: hardness—high: (A) feed for rabbits (NRT-1S, Nisseiken Co.), hardness—medium: (B) feed for swine (synthetic milk for late term, Nihon Haigo Shiryo Co.) and hardness—somewhat low: (C) feed for chickens (chicken feed, Nihon Haigo Shiryo Co.)

The hardness of the pellets was measured using a Monsant hardness meter. The results are shown in Table 8, in which the decrease in viable count in all samples was significantly improved as compared with the decrease in viable count in the control group after pelleting. Specifically, high hardness pellets show significantly improved viable counts in the samples 7-a-, 7-b and 7-c.

Accordingly, the stability of viable microorganisms in the pelleting process with feed was shown to be significantly improved in the powdered composition obtained by spray-drying the mixture of starch in excess of 0.01 part, preferably over 0.1 part per one part by weight of microbial cells.

TABLE 8

| Sample No. | Feed | pellet hardness (kg) | Viable count in mash (cells/g) | Viable count in pellet (cells/g) | Viable ratio (%) |
|---|---|---|---|---|---|
| 7-a | A | 9.5 | $1.14 \times 10^6$ | $0.941 \times 10^6$ | 83 |
|  | B | 8.3 | $1.07 \times 10^6$ | $0.907 \times 10^6$ | 85 |
|  | C | 5.4 | $1.17 \times 10^6$ | $0.992 \times 10^6$ | 85 |
| 7-b | A | 10.9 | $1.02 \times 10^6$ | $0.836 \times 10^6$ | 82 |

TABLE 8-continued

| Sample No. | Feed | pellet hardness (kg) | Viable count in mash (cells/g) | Viable count in (cells/g) | Viable ratio (%) |
|---|---|---|---|---|---|
| | B | 6.4 | $1.02 \times 10^6$ | $0.888 \times 10^6$ | 87 |
| | C | 5.1 | $0.978 \times 10^6$ | $0.886 \times 10^6$ | 91 |
| 7-c | A | 10.2 | $1.08 \times 10^6$ | $0.882 \times 10^6$ | 82 |
| | B | 8.1 | $1.07 \times 10^6$ | $0.903 \times 10^6$ | 84 |
| | C | 5.7 | $1.03 \times 10^6$ | $1.02 \times 10^6$ | 99 |
| 7-d | A | 11.0 | $1.23 \times 10^6$ | $0.861 \times 10^6$ | 70 |
| | B | 7.4 | $1.22 \times 10^6$ | $1.02 \times 10^6$ | 84 |
| | C | 6.4 | $1.10 \times 10^6$ | $1.00 \times 10^6$ | 91 |
| Control-2 | A | 9.7 | $1.17 \times 10^6$ | $0.515 \times 10^6$ | 44 |
| | B | 7.0 | $1.01 \times 10^6$ | $0.566 \times 10^6$ | 56 |
| | C | 5.4 | $1.38 \times 10^6$ | $1.09 \times 10^6$ | 79 |

EXAMPLE 9

Wheat flour (protein content 9.3–9.5%, Daiya, trade name, Nihon Seifun Co.) was suspended in a spore-cell suspension of *Bacillus toyoi* (Toyocerin) at the compositions illustrated in Table 9 and spray-dried to obtain powdered viable microorganism compositions. In this example the process was carried out the same way as in Example 7.

TABLE 9

| Sample No. | cell suspension (l) (): cell weight (kg) | Base (kg) | Ratio of cell:base | Viable count in dried powder (cells/g) |
|---|---|---|---|---|
| 9-a | 10 (1) | 1 | 1:1 | $13.2 \times 10^{10}$ |
| 9-b | 10 (1) | 0.5 | 1:0.5 | $15.5 \times 10^{10}$ |
| 9-c | 10 (1) | 0.1 | 1:0.1 | $16.5 \times 10^{10}$ |
| 9-d | 10 (1) | 0.01 | 1:0.01 | $17.2 \times 10^{10}$ |

EXAMPLE 10

Samples obtained in Example 9 were pelleted by the same process as in Example 8. The viable count was measured and compared with that of the mash for checking the stability of the viable microorganisms, and the same results were obtained as for starch in Example 8. The results are shown in Table 10.

TABLE 10

| Sample No. | Feed | pellet hardness (kg) | Viable count in mash (cells/g) | Viable count in pellet (cells/g) | Viable ratio (%) |
|---|---|---|---|---|---|
| 9-a | A | 8.6 | $0.946 \times 10^6$ | $0.870 \times 10^6$ | 92 |
| | B | 6.0 | $0.950 \times 10^6$ | $0.856 \times 10^6$ | 90 |
| | C | 5.3 | $1.03 \times 10^6$ | $0.952 \times 10^6$ | 92 |
| 9-b | A | 9.2 | $1.03 \times 10^6$ | $0.921 \times 10^6$ | 89 |
| | B | 6.7 | $1.04 \times 10^6$ | $0.953 \times 10^6$ | 92 |
| | C | 5.7 | $1.13 \times 10^6$ | $1.09 \times 10^6$ | 96 |
| 9-c | A | 7.5 | $1.25 \times 10^6$ | $1.09 \times 10^6$ | 87 |
| | B | 6.2 | $1.35 \times 10^6$ | $1.27 \times 10^6$ | 94 |
| | C | 5.5 | $1.22 \times 10^6$ | $1.14 \times 10^6$ | 93 |
| 9-d | A | 8.7 | $1.39 \times 10^6$ | $1.01 \times 10^6$ | 73 |
| | B | 5.8 | $1.16 \times 10^6$ | $0.961 \times 10^6$ | 83 |
| | C | 5.4 | $1.13 \times 10^6$ | $1.02 \times 10^6$ | 90 |
| Control-2 | A | 9.7 | $1.17 \times 10^6$ | $0.515 \times 10^6$ | 44 |
| | B | 7.0 | $1.01 \times 10^6$ | $0.566 \times 10^6$ | 56 |
| | C | 5.4 | $1.38 \times 10^6$ | $1.09 \times 10^6$ | 79 |

EXAMPLE 11

Soybean flour (Sunrich Flour Showa, trade name, Showa Sangyo Co.), which was produced by soybean seeds being defatted, dried and crushed to pass an 80 mesh sieve, was suspended with a spore-cell suspension of *Bacillus toyoi* (Toyocerin) at the concentrations set forth in Table 11 and spray-dried to obtain powdered viable microorganism compositions. In this example the process was carried out in the same way as in Example 7. Then lactose (sample 11-e, Pharmatose, trade name, Demelkindustrie Veghel B.V., importer-Iwaki Co.) was suspended in water and spray-dried in the same way as hereinabove.

TABLE 11

| Sample No. | Cell suspension (l) (): cell weight (kg) | Base (kg) | Ratio of cells: base | Viable count in dried powder (cells/g) |
|---|---|---|---|---|
| 11-a | 10 (1) | 1 | 1:1 | $11.6 \times 10^{10}$ |
| 11-b | 10 (1) | 0.5 | 1:0.5 | $14.3 \times 10^{10}$ |
| 11-c | 10 (1) | 0.1 | 1:0.1 | $16.0 \times 10^{10}$ |
| 11-d | 10 (1) | 0.01 | 1:0.01 | $17.5 \times 10^{10}$ |
| 11-e | 10 (1) | 0.5 | 1:0.5 | $14.0 \times 10^{10}$ |

EXAMPLE 12

Samples obtained in Example 11 were pelleted by the same process as in Example 8. The viable count was measured and compared with that of the mash for checking the stability of the viable microorganisms, and substantially the same results were obtained as for starch in Example 8. No improved results were observed in the case of lactose (sample 11-e in the Table). The results are shown in Table 12.

TABLE 12

| Sample No. | Feed | Pellet hardness (kg) | Viable count in mash (cells/g) | Viable count in pellet (cells/g) | Viable ratio (%) |
|---|---|---|---|---|---|
| 11-a | A | 8.8 | $1.16 \times 10^6$ | $1.14 \times 10^6$ | 98 |
| | B | 5.7 | $1.05 \times 10^6$ | $0.996 \times 10^6$ | 95 |
| | C | 5.2 | $1.07 \times 10^6$ | $1.04 \times 10^6$ | 97 |
| 11-b | A | 9.4 | $1.04 \times 10^6$ | $0.915 \times 10^6$ | 88 |
| | B | 6.4 | $0.940 \times 10^6$ | $0.885 \times 10^6$ | 94 |
| | C | 4.5 | $1.23 \times 10^6$ | $1.22 \times 10^6$ | 99 |
| 11-c | A | 8.7 | $0.951 \times 10^6$ | $0.857 \times 10^6$ | 90 |
| | B | 6.1 | $1.06 \times 10^6$ | $0.902 \times 10^6$ | 85 |
| | C | 5.2 | $1.11 \times 10^6$ | $0.933 \times 10^6$ | 84 |
| 11-d | A | 8.2 | $1.16 \times 10^6$ | $0.823 \times 10^6$ | 71 |
| | B | 6.6 | $1.03 \times 10^6$ | $0.840 \times 10^6$ | 82 |
| | C | 5.0 | $1.11 \times 10^6$ | $0.922 \times 10^6$ | 83 |
| Control-2 | A | 9.7 | $1.17 \times 10^6$ | $0.515 \times 10^6$ | 44 |
| | B | 7.0 | $1.01 \times 10^6$ | $0.566 \times 10^6$ | 56 |
| | C | 5.4 | $1.38 \times 10^6$ | $1.09 \times 10^6$ | 79 |
| 11-e | B | 5.7 | $1.35 \times 10^6$ | $0.830 \times 10^6$ | 61 |

EXAMPLE 13

Starch (refer to Example 7), corn flour (refer to Example 9), soybean flour (refer to Example 11) and hydroxypropyl methylcellulose (TC-5, Shinetsu Chem. Co.), each 2 g, suspended in water (200 ml) were heated at 85° C. to pregelatinize the suspension. The gelatinized liquids were cooled and kneaded well with admixed cells of *Bacillus toyoi* (20 g, $2.5 \times 10^{10}$ cells/g), then spread on a plate and dried by blowing at room temperature. The dried products were crushed in a speed-mill and subsequently granulated in an oscillating granulator (32 mesh, oscillator) to prepare viable microorganism compositions.

The results are shown in Table 13. Note that carboxymethyl ethylcellulose shows no tendency toward stabilization, and the same is true for hydroxypropyl methylcellulose.

TABLE 13

| Sample No. | cell weight (g) | Base substance | weight (g) | Ratio of cells:base | Viable count in dried powder (cells/g) |
|---|---|---|---|---|---|
| 13-a | 20 | starch | 2 | 1:0.1 | $17.5 \times 10^{10}$ |
| 13-b | 20 | wheat flour | 2 | 1:0.1 | $18.8 \times 10^{10}$ |
| 13-c | 20 | soybean flour | 2 | 1:0.1 | $17.0 \times 10^{10}$ |
| 13-d | 20 | hyroxy-methyl-cellulose | 2 | 1:0.1 | $16.8 \times 10^{10}$ |

EXAMPLE 14

Samples obtained in Example 13 was pelleted by the same process as in Example 8 to produce pellets. The viable count was measured and compared with that of the mash for checking the stability of the viable microorganisms.

The results are shown in Table 14. The stability of samples 13-a, 13-b and 13-c, which were the samples using a pasty liquid of pre-heated gelatinized base, was observed to be improved as compared with control samples in the pelleting process. Contrary to that, the stability of sample 13-d was not so improved.

TABLE 14

| Sample No. | Feed | Pellet hardness (kg) | Viable count in mash (cells/g) | Viable count in Pellet (cells/g) | Viable ratio (%) |
|---|---|---|---|---|---|
| 13-a | A | 8.8 | $1.28 \times 10^6$ | $1.11 \times 10^6$ | 87 |
|  | B | 7.4 | $1.12 \times 10^6$ | $1.14 \times 10^6$ | 102 |
|  | C | 4.7 | $0.998 \times 10^6$ | $0.889 \times 10^6$ | 89 |
| 13-b | A | 9.2 | $1.31 \times 10^6$ | $1.21 \times 10^6$ | 92 |
|  | B | 6.8 | $1.09 \times 10^6$ | $0.937 \times 10^6$ | 86 |
|  | C | 5.7 | $1.03 \times 10^6$ | $0.989 \times 10^6$ | 96 |
| 13-c | A | 10.0 | $0.983 \times 10^6$ | $0.806 \times 10^6$ | 82 |
|  | B | 6.5 | $1.26 \times 10^6$ | $1.17 \times 10^6$ | 93 |
|  | C | 5.2 | $1.31 \times 10^6$ | $1.27 \times 10^6$ | 97 |
| Control-2 | A | 9.7 | $1.17 \times 10^6$ | $0.515 \times 10^6$ | 44 |
|  | B | 7.0 | $1.01 \times 10^6$ | $0.566 \times 10^6$ | 56 |
|  | C | 5.4 | $1.38 \times 10^6$ | $1.09 \times 10^6$ | 79 |
| 13-d | A | 8.4 | $1.15 \times 10^6$ | $0.624 \times 10^6$ | 54 |

What is claimed is:

1. A process for production of feed pellets containing a stabilized spore-forming microorganism composition, said process comprising drying by spray-drying or air-drying after kneading, a carbohydrate component consisting essentially of starch, and spore-forming viable microorganisms belonging to species *Bacillus toyoi* in admixture in a non-toxic aqueous medium, said starch and said microorganisms being present in said medium in a weight ratio from 0.01 to 100 parts of said starch to one part of said microorganisms; admixing said composition with animal feed to form a feed mixture, and pelleting said feed mixture with steam and pressure to form pellets of said feed mixture.

2. A process according to claim 1 wherein said starch is corn starch.

3. A process according to claim 1 wherein said starch is from a member selected from the group consisting of rice, wheat, barley, rye, oats and soybeans.

4. A process according to claim 1 wherein said starch is from a tuberous root, tuber or corm.

5. A process according to claim 1 wherein said component is heat treated.

6. A process according to claim 5 wherein said component is pre-heat-treated.

7. A process according to claim 5 wherein said heat-treatment is heat-drying.

* * * * *

UNITED STATES PATENT AND TRADEMARK OFFICE
CERTIFICATE OF CORRECTION

PATENT NO. : 5,283,059
DATED : February 1, 1994
INVENTOR(S) : Masaki SUZUKI et al.

It is certified that error appears in the above—identified patent and that said Letters Patent is hereby corrected as shown below:

On title page, item [54] and col. 1, line 2, change "STORE" to --SPORE--.

Signed and Sealed this

Fifth Day of July, 1994

*Attest:*

BRUCE LEHMAN

*Attesting Officer*     *Commissioner of Patents and Trademarks*